United States Patent [19]

Houston et al.

[11] Patent Number: 5,634,927
[45] Date of Patent: Jun. 3, 1997

[54] SIZING PLATE AND DRILL GUIDE ASSEMBLY FOR ORTHOPAEDIC KNEE INSTRUMENTATION

[75] Inventors: Michelle L. Houston, Warsaw; Steven A. Zawadzki, Pierceton, both of Ind.

[73] Assignee: Zimmer, Inc., Warsaw, Ind.

[21] Appl. No.: 499,049

[22] Filed: Jul. 6, 1995

[51] Int. Cl.$^6$ ................................................ A61K 606/96
[52] U.S. Cl. .................... 606/96; 606/79; 606/80; 606/88
[58] Field of Search .................... 606/88, 89, 96, 606/87, 79, 80

[56] References Cited

U.S. PATENT DOCUMENTS

| | | | |
|---|---|---|---|
| D. 274,094 | 5/1984 | Kenna | D24/26 |
| 4,357,716 | 11/1982 | Brown | 3/1.913 |
| 4,524,766 | 6/1985 | Petersen | 128/92 H |
| 4,736,737 | 4/1988 | Fargie et al. | 128/92 VY |
| 4,787,383 | 11/1988 | Kenna | 128/303 R |
| 4,791,919 | 12/1988 | Elloy et al. | 128/92 VW |
| 4,822,362 | 4/1989 | Walker et al. | 623/20 |
| 4,822,365 | 4/1989 | Walker et al. | 623/20 |
| 4,936,853 | 6/1990 | Fabian et al. | 623/20 |
| 4,985,037 | 1/1991 | Petersen | 623/20 |
| 5,002,547 | 3/1991 | Poggie et al. | 606/88 |
| 5,002,581 | 3/1991 | Paxson et al. | 623/23 |
| 5,047,061 | 9/1991 | Brown | 623/23 |
| 5,053,037 | 10/1991 | Lackey | 606/79 |
| 5,062,852 | 11/1991 | Dorr et al. | 623/20 |
| 5,098,436 | 3/1992 | Ferrante et al. | 606/87 |
| 5,100,408 | 3/1992 | Lackey | 606/79 |
| 5,108,396 | 4/1992 | Lackey et al. | 606/62 |
| 5,112,336 | 5/1992 | Krevolin et al. | 606/96 |
| 5,116,338 | 5/1992 | Poggie et al. | 606/90 |
| 5,133,760 | 7/1992 | Petersen et al. | 623/20 |
| 5,135,529 | 8/1992 | Paxson et al. | 606/85 |
| 5,141,513 | 8/1992 | Fortune et al. | 606/96 |
| 5,201,882 | 4/1993 | Paxson | 623/23 |
| 5,250,050 | 10/1993 | Poggie et al. | 606/79 |
| 5,271,737 | 12/1993 | Baldwin et al. | 623/20 |
| 5,275,603 | 1/1994 | Ferrante et al. | 606/86 |
| 5,282,803 | 2/1994 | Lackey | 606/80 |
| 5,282,866 | 2/1994 | Cohen et al. | 623/20 |
| 5,290,313 | 3/1994 | Heldreth | 623/20 |
| 5,312,411 | 5/1994 | Steele et al. | 606/88 |
| 5,342,367 | 8/1994 | Ferrante et al. | 606/86 |
| 5,344,423 | 9/1994 | Dietz et al. | 606/87 |
| 5,356,414 | 10/1994 | Cohen et al. | 606/88 |
| 5,411,505 | 5/1995 | Mumme | 606/88 |
| 5,417,695 | 5/1995 | Axelson, Jr. | 606/89 |
| 5,534,005 | 7/1996 | Tokish, Jr. et al. | 606/96 |

FOREIGN PATENT DOCUMENTS

WO94/05211  3/1994  WIPO.

OTHER PUBLICATIONS

Howmedica—Duraconcept—Design Concepts of the Duracon Total knee System—©1993.
Johnson & Johnson Orthopaedics—P.F.C. Modular Knee System w/Specialist Instruments—No date available.
Smith & Nephew Richards Inc.—Genesis Total Knee System—No date available.
Zimmer—Porous MG II Total Knee—Cross-Stemmed Tibial Tray—lit. #97-8510-05—©1992.
Zimmer, Inc.—State-of-the-Art Revision Instrumentation—1994.

*Primary Examiner*—Michael Buiz
*Assistant Examiner*—Julian W. Woo
*Attorney, Agent, or Firm*—Margaret L. Geringer

[57] ABSTRACT

The invention is directed to an orthopaedic instrumentation assembly 10 for at least partially preparing an end of a bone with a drill for receiving a prosthesis. The instrumentation assembly includes a drill guide 14 having a drill guide opening for guiding a drill into the bone; and an orthopaedic sizing plate 12 attachable to the end of the bone. The sizing plate 12 is configured for interconnecting with the drill guide 14. The drill guide 14 includes a first drill stop 47 and the sizing plate includes a second drill stop 33, with the first drill stop and the second drill stop coacting with each other for limiting projection and for maintaining axial alignment of the drill into the bone.

6 Claims, 2 Drawing Sheets

SIZING PLATE AND DRILL GUIDE ASSEMBLY FOR ORTHOPAEDIC KNEE INSTRUMENTATION

BACKGROUND OF THE INVENTION

1. Field of the Invention

The present invention relates to orthopaedic instrumentation, and, more particularly, to orthopaedic instrumentation for preparing the proximal end of a tibia for receiving a prosthesis.

2. Description of the Related Art

Orthopaedic instrumentation may include, e.g., a sizing plate which is attached to an end of a bone. The size of the sizing plate corresponds to the size of a prosthesis which is to be mated with the bone; and the positioning of the sizing plate determines the location of subsequent bone shaping steps to be made to the end of the bone to prepare the bone for receiving the prosthesis. The sizing plate may be configured to interconnect with a drill guide used in drilling operations on the bone. When the sizing plate is used in conjunction with an end of a tibia, such drilling operations may include forming a recess for receiving a prosthetic stem, as well as forming recesses for receiving pegs, such as posterior pegs.

It is also known to use a broach assembly to form cuts in the end of a bone. For example, if openings are formed in a tibia as indicated above to receive a prosthetic stem and posterior pegs, the broach may be used to cut respective fin openings extending from the stem opening. The fin openings formed with the broach matingly receive fins which extend from the stem on a tibial prosthesis provisional and/or implant.

What is needed in the art is an instrumentation assembly for shaping an end of a bone including a sizing plate which is attachable to and allows the use of either a drill guide or a broach.

What is further needed in the art is an instrumentation assembly including a tibial sizing plate which is attachable to a drill guide, and which is configured to limit projection of a drill into the end of a bone.

SUMMARY OF THE INVENTION

The present invention is directed to an orthopaedic instrumentation assembly including a tibial sizing plate and a drill guide attachable to each other, wherein each of the tibial sizing plate and drill guide include respective drill stops which coact with each other for limiting projection of a drill into the tibia.

The invention comprises, in one form thereof, an orthopaedic instrumentation assembly for at least partially preparing an end of a bone with a drill for receiving a prosthesis. The instrumentation assembly includes a drill guide having a drill guide opening for guiding a drill into the bone; and an orthopaedic sizing plate attachable to the end of the bone. The sizing plate is configured for interconnecting with the drill guide. The drill guide includes a first drill stop and the sizing plate includes a second drill stop, with the first drill stop and the second drill stop coacting with each other for limiting projection of the drill into the bone.

An advantage of the present invention is that a tibial sizing plate can be simultaneously configured to accommodate a drill, such as a stem drill and/or peg drill, as well as a broach for forming fin cuts in the proximal end of the tibia.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein.

Corresponding reference characters indicate corresponding parts throughout the several views. The exemplifications set out herein illustrate one preferred embodiment of the invention, in one form, and such exemplifications are not to be construed as limiting the scope of the invention in any manner.

DETAILED DESCRIPTION OF THE INVENTION

Figure 1:
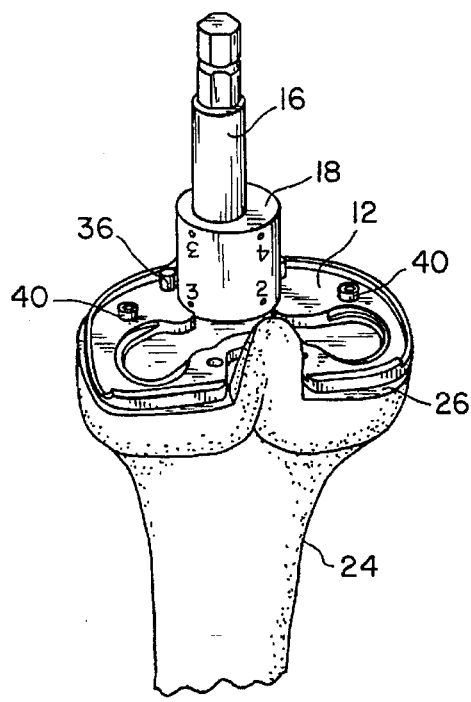
FIG. 1 is a perspective view of an embodiment of a tibial sizing plate of the present invention disposed against a tibia, with the tibial sizing plate connected to a bushing disposed about an intramedullary reamer.
Figure 2:
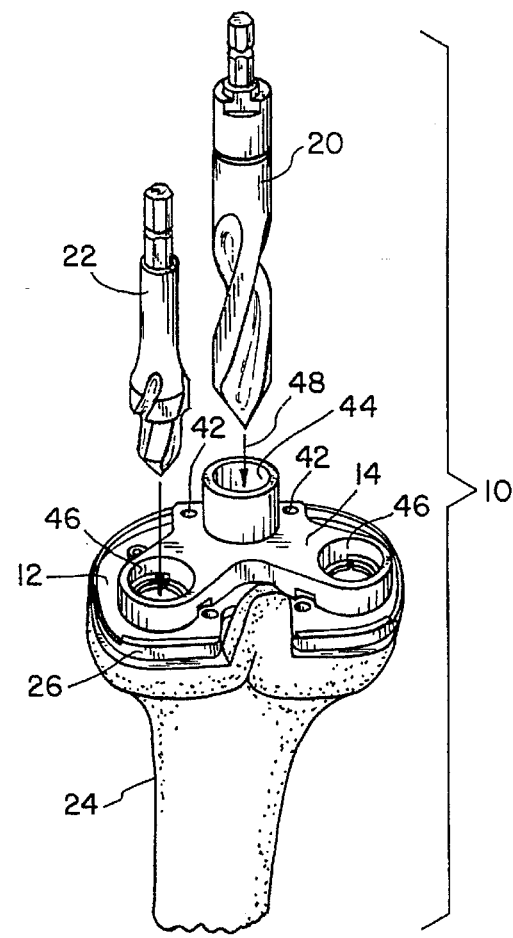
FIG. 2 is a perspective view of the tibial sizing plate shown in FIG. 1, with an embodiment of a drill guide of the present invention attached thereto, and a stem drill and peg drill disposed thereabove.

Referring now to the drawings, and particularly to FIGS. 1 and 2, an orthopaedic instrumentation assembly 10 of the present invention includes a plate member 12 and drill guide 14. Other parts associated with instrumentation assembly 10 also include an intramedullary (IM) member 16, bushing 18, stem drill 20 and peg drill 22.

IM member 16 (FIG. 1), such as an IM reamer, is attached to a bone 24. In the embodiment shown, bone 24 is a tibia, and IM member 16 is disposed within an IM canal 23 (FIGS. 7 and 8) of tibia 24. Tibia 24 includes a proximal end 26 which has been previously shaped using appropriate instrumentation, such as cutting instrumentation.

Figure 3:
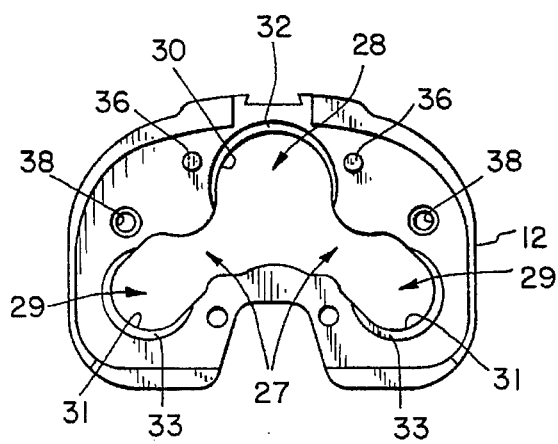
FIG. 3 is a top view of the tibial sizing plate shown in FIGS. 1 and 2.
Figure 4:
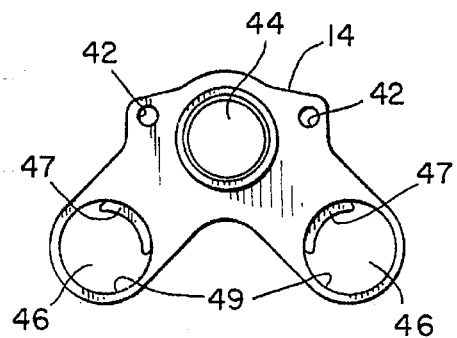
FIG. 4 is a top view of the drill guide shown in FIG. 2.

Plate member 12 is constructed as a tibial sizing plate in the embodiment shown, and includes a stem opening 28 therein defining an inner periphery 30 thereof. A recessed shoulder 32 (FIG. 3) is disposed within stem opening 28 and about inner periphery 30. A pair of peg openings 29 each have an inner periphery 31 thereof. A shoulder 33 extends partially around each respective inner periphery 31. Each peg opening 29 is disposed in communication with stem opening 28. That is, peg openings 29 are not discretely formed relative to stem opening 28, but are interconnected to stem openings 28 by a groove or connecting opening 27 or the like. Tibial sizing plate 12 also includes a bottom surface 34 (FIG. 6) which is adapted for placement against proximal end 26 of tibia 24. Tibial sizing plate 12 further includes locating pins 36 adapted for engagement with a drill guide (to be discussed hereinafter), and holes 38 (FIGS. 3 and 5) for receiving respective fixation pins 40 (FIG. 1).

Bushing 18 (FIG. 1) is sized and configured for placement within stem opening 28 and against recessed shoulder 32 of tibial sizing plate 12. Bushing 18 has a bore (not numbered) extending therethrough for receiving IM reamer 16. In an assembled position, IM member 16 is disposed within the bore of bushing 18. The bushing 18 may be an offset bushing (as shown) or a symmetrical bushing (not shown).

Figure 5:
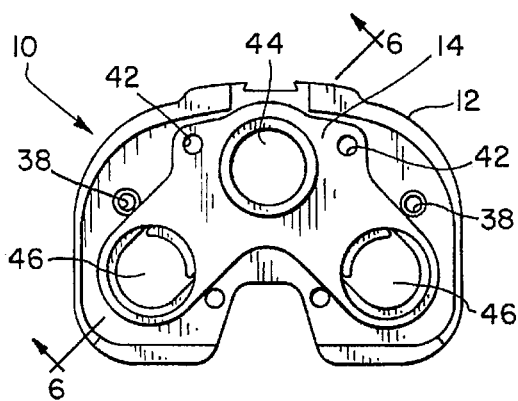
FIG. 5 is a top view of the drill guide and tibial sizing plate shown in FIGS. 2–4, in an assembled position.
Figure 6:
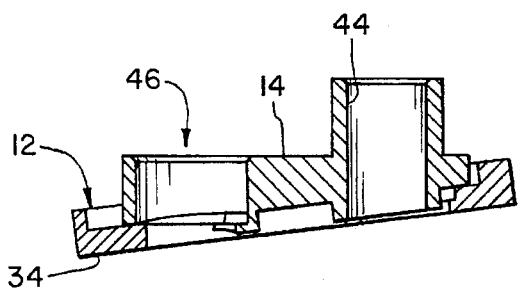
FIG. 6 is a side, sectional view taken along line 6–6 of FIG. 5.

Drill guide 14 is connectable with tibial sizing plate 12. More particularly, drill guide 14 includes holes 42 which are sized for receiving locating pins 36 (FIGS. 1 and 3) therein. Locating pins 36 and holes 42 define an interconnecting structure therebetween and prevent relative translatory movement between drill guide 14 and tibial sizing plate 12. Drill guide 14 further includes a stem drill guide opening 44 and tibial peg drill guide openings 46. When in an assembled position, as shown in FIGS. 2, 5, and 6, stem drill guide opening 44 is associated with stem opening 28, and tibial peg drill guide openings 46 are respectively associated with peg openings 29. Stem drill guide opening 44 is sized to receive stem drill 20 therein, such as indicated by directional arrow 48. Stem drill guide opening 44 guides stem drill 20 such that a recess 23 (FIGS. 7 and 8) can be formed within tibia 24 for receipt of a prosthetic stem. Tibial peg drill guide openings 46 guide a peg drill 22 to form openings 25 (FIGS. 7 and 8) in tibia proximal end 26 for receipt of posterior extending pegs on a tibial prosthesis. A shoulder 47 is disposed within each tibial peg drill guide opening 46, and extends partially around an inner periphery 49 thereof.

In the embodiment shown in FIGS. 1–6, drill guide 14 includes a first drill stop defined by shoulder 47; and tibial sizing plate 12 includes a second drill stop defined by shoulder 33. Shoulder 47 and shoulder 33 define first and second shoulders which coact with each other for limiting projection of peg drill 22 into tibia 24. Shoulder 47, which coacts with shoulder 33, is beneficial and provides a supplemental stop to help prevent tilting of peg drill 22, thus maintaining axial alignment of the peg drill 22, since shoulder 33 is not a full circumferential shoulder, but rather a partial circumferential shoulder, due to the interconnecting opening 27 between peg opening 29 and stem opening 28. This interconnecting opening 27 enables the same tibial sizing plate 12 to accommodate the broach 54 for cutting fin openings 66 with cutting head 56, as well as to accommodate the drill guide 14. The shoulder 47 thus provides a supplemental stop which complements the partial circumferential shoulder 33.

However, it is also possible that, depending upon the depth of peg drill guide openings 46, the radial tolerance between peg drill 22 and drill guide openings 46, etc., the shoulder 33 of tibial sizing plate 12 may be sufficient to provide the drill stop and restrict the peg drill 22 from tilting without the necessity for first shoulder 47 of drill guide 14.

Figure 7:
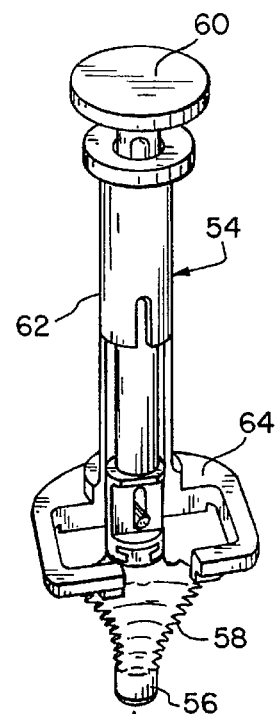
FIG. 7 is a perspective view of the tibial sizing plate shown in FIGS. 1–3 and 5–6, with a broach impactor assembly disposed thereabove.
Figure 7:
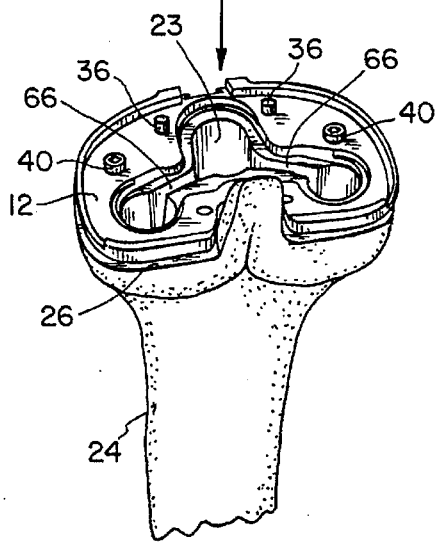
Figure 8:
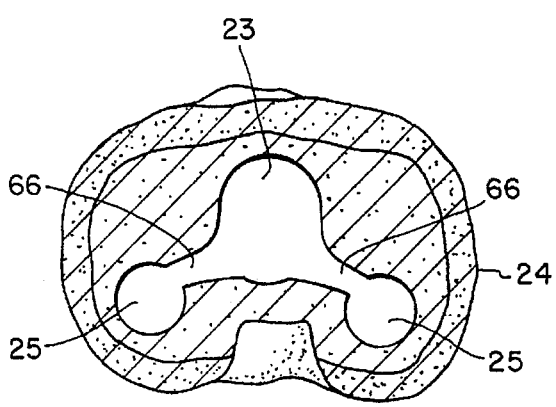
FIG. 8 is a top view of a tibia prepared with the embodiment of the tibial sizing plate and drill guide shown in FIGS. 1–7.

Referring now to FIGS. 7 and 8, a broach assembly 52 including tibial sizing plate 12 of the present invention is shown. Broaching assembly 52 includes a broach 54 having a cutting head 56 with teeth 58. Cutting head 56 is connected to an impact end 60, and slidable relative to a housing 62. A platform 64 includes openings (not shown) on the underside thereof which are sized and located to receive locating pins 36 extending from tibial sizing plate 12. Platform 64 may thus be engaged with tibial sizing plate 12 by the interconnection between locating pins 36 and the openings in platform 64, such that no translatory movement occurs between broach 54 and tibial sizing plate 12 when connected. When broach 54 is assembled with tibial sizing plate 12, a mallet or the like is used to strike impact end 60, and thereby drive cutting head 56 into tibia 24 to cut fin openings 66 in tibia 24. Fin openings 66 are configured to receive corresponding fins which extend from the stem on a tibial prosthesis (not shown).

Using orthopaedic instrumentation assembly 10 of the present invention as described above, it is possible to provide a tibial sizing plate which simultaneously limits projection of a drill into a tibia, while at the same time allowing use of a broach for cutting a fin opening extending from the IM canal toward or to the posterior peg openings. It is thus possible to use a single plate member for both the drilling and fin broaching operations.

In use, IM reamer 16 is inserted into IM canal 23 of tibia 24 in a known fashion. Thereafter, tibial sizing plate 12 is positioned over reamer 16, whereby IM reamer 16 extends through stem opening 28. Tibial sizing plate 12 is positioned such that bottom surface 34 thereof is disposed against proximal end 26 of tibia 24. Bushing 18 is then slid over IM reamer 16, whereby IM reamer 16 extends through the bore therein. Bushing 18 is then removably attached to tibial sizing plate 12, such that bushing 18 is disposed partially within stem opening 28 and against recessed shoulder 32. When using bushing 18 having the offset bore, as shown in FIG. 1, tibial sizing plate 12 is then moved in a translatory direction with respect to IM reamer 16, thereby causing a rotational movement of bushing 18. After proper positioning, tibial sizing plate 12 is attached to tibia 24 using fixation pins 40. Bushing 18 and IM reamer 16 are then removed, and drill guide 14 (FIG. 4) is attached to tibial sizing plate by aligning locating pins 36 with holes 42. If the bushing 18 having the symmetrical bore (not shown) is used, use of stem drill 20 is optional. If desirable, stem drill 20 can be slidingly received within stem drill guide opening 44 and used to enlarge IM canal 23 in tibia 24 for receipt of a stem of a tibial prosthesis. Alternatively, when the bushing 18 having the offset bore, as shown in FIG. 1, is used, stem drill 20 can be used to form a recess (not shown) in tibia 24 which is disposed offset from and in communication with IM canal 23 for receipt of an offset prosthetic stem. Peg drill 22 is then respectively received within each of peg drill guide openings 46 and used to form recesses 25 in tibia 24 for receipt of posterior extending pegs on a tibial prosthesis. Drill guide 14 is then removed from tibial sizing plate 12. Thereafter, broach 54 is attached to tibial sizing plate 12 and used to cut fin openings 66 extending from IM canal 23 toward or to posterior peg openings 25. Broach 54 and tibial sizing plate 12 are then detached from tibia 24 and the tibial prosthesis provisional and then subsequently the tibial implant is installed in the prepared bone.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An orthopaedic instrumentation assembly for at least partially preparing an end of a bone with a drill for receiving a prosthesis, said instrumentation assembly comprising:

a drill guide including a drill guide opening for guiding a drill into the bone; and an orthopaedic plate member attachable to the end of the bone, said plate member including means for interconnecting with said drill guide;

wherein said drill guide includes a first drill stop means and said orthopaedic plate member includes a second drill stop means, said first drill stop means and said second drill stop means coacting with each other for limiting projection and for maintaining axial alignment of the drill into the bone, and wherein said first drill stop means comprises a first shoulder on said drill guide, and said second drill stop means comprises a second shoulder on said plate member, and wherein said plate member includes a drill opening associated with said drill guide opening, and wherein said first shoulder is disposed at an inner periphery of said drill guide opening, and said second shoulder is disposed at an inner periphery of said drill opening, and wherein said drill opening of said plate member includes an interconnecting opening extending therefrom, such that the second shoulder on the inner periphery of the drill opening of said plate member forms only a partial circumferential shoulder, and wherein the first shoulder on the inner periphery of said drill guide opening of said drill guide provides a supplemental stop which complements the partial circumferential shoulder of the drill opening on said plate member, said first shoulder of said drill guide being positioned within the interconnecting opening of said plate member.

2. The orthopaedic instrumentation assembly of claim 1, wherein said interconnecting opening on said plate member defines an opening for receiving a fin cutting member of a broach when said drill guide is not interconnected with said plate member.

3. The orthopaedic instrumentation assembly of claim 1, wherein said orthopaedic plate member comprises a tibial sizing plate.

4. The orthopaedic instrumentation assembly of claim 1, wherein said drill guide includes a pair of locating holes, and wherein said interconnecting means comprises a pair of locating pins connected to said plate member and respectively received within said locating holes.

5. An orthopaedic instrumentation assembly for at least partially preparing a proximal end of a tibia for receiving a prosthesis, said instrumentation assembly comprising:

a drill guide including at least one peg drill guide opening for guiding a peg drill; and a tibial sizing plate attachable to the proximal end of the tibia and including means for interconnecting with said drill guide, said sizing plate having at least one peg opening, each said peg opening associated with a respective said peg drill guide opening, said sizing plate including a first drill stop means, and said drill guide including a supplemental drill stop for coacting with the first drill stop means for limiting projection and for maintaining axial alignment of the peg drill into the tibia, and wherein said drill stop means comprises a shoulder on said sizing plate and said shoulder is disposed at an inner periphery of said peg opening, and wherein said supplemental drill stop comprises a supplemental shoulder on said drill guide and said supplemental shoulder is disposed on an inner periphery of a drill guide opening on said drill guide, and wherein said peg opening of said sizing plate includes an interconnecting opening extending therefrom, such that the sizing plate shoulder on the inner periphery of the peg opening forms only a partial circumferential shoulder, and wherein the supplemental shoulder on the inner periphery of said drill guide opening of said drill guide provides a supplemental stop which complements the partial circumferential shoulder of the peg opening on said sizing plate, said supplemental shoulder of said drill guide being positioned with the interconnecting opening of said sizing plate.

6. The orthopaedic instrumentation assembly of claim 5, wherein said drill guide includes a pair of locating holes, and wherein said interconnecting means comprises a pair of locating pins connected to said tibial sizing plate and respectively received within said locating holes.

* * * * *